(12) United States Patent
Tomi et al.

(10) Patent No.: US 6,866,872 B1
(45) Date of Patent: Mar. 15, 2005

(54) WITHANIA SOMNIFERA DUNAL EXTRACTS FOR INCREASING MALE SPERM COUNT

(75) Inventors: Hironori Tomi, Shiga (JP); Masaru Yoshida, Kyoto (JP); Kouichi Kishida, Kyoto (JP)

(73) Assignee: Nippon Shinyaku Co., Ltd. (JP)

( * ) Notice: Subject to any disclaimer, the term of this patent is extended or adjusted under 35 U.S.C. 154(b) by 0 days.

(21) Appl. No.: 10/031,650

(22) PCT Filed: May 9, 2000

(86) PCT No.: PCT/JP00/02940

§ 371 (c)(1),
(2), (4) Date: Nov. 9, 2001

(87) PCT Pub. No.: WO00/67768

PCT Pub. Date: Nov. 16, 2000

(30) Foreign Application Priority Data

May 10, 1999 (JP) ............................................ 11-128335

(51) Int. Cl.$^7$ ................................................ A61K 35/78
(52) U.S. Cl. ........................ 424/725; 424/773; 424/774
(58) Field of Search ................................ 424/773, 774, 424/195.1, 725

(56) References Cited

U.S. PATENT DOCUMENTS 5,683,698 A * 11/1997 Chavali et al. .......... 424/195.1

OTHER PUBLICATIONS

Abdel–Magied et al. The Effect of Aqueous Extracts of Cynomorium Coccineum and *Withania somnifera* on Testicular Development in Immature Wistar Rats; Journal of Ethnopharmacology 75 (2001) pp. 1–4.*
Garg et al. Effect of *Withania somnifera* on Reproduction In Mice; Planta Med. (1965) 13, pp. 46–47.*
Revilla et al. Comparison of Several Procedures Used for the Extraction of Anthocyanins From Red Grapes; J. Agric. Food Chem. (1998), 46, pp. 4592–4597.*
Rao et al. Effects of Some Indigenous Drug on The Sexual Behavior of Male Rats; Indian Journal of Pharm. Sciences (1978) 40, No. 6 p. 236–237.*
Farnsworth, N.R. et al., "Current Status of Plant Products Reported to Inhibit Sperm." Research Frontiers in Fertility Regulation. vol. 2, No. 1, Jun. 1982, pp. 1–16.
Abstract of Shappira, Z. et al., "Preliminary Studies on the Potential of Some Indigenous Medicinal Plants to Regulate Reproduction in White Rats." Israel Journal of Botany Basic and Applied Plant Sciences, vol. 36, No. 4, 1987, p. 212.

* cited by examiner

*Primary Examiner*—Patricia Patten
(74) *Attorney, Agent, or Firm*—Greenberg Traurig LLP; Eugene C. Rzucidlo

(57) ABSTRACT

The object of the present invention is to provide a composition comprising a *Withania somnifera* extract. Another object of the invention is to provide a method for increasing male sperm count in-vivo with a composition comprising *Withania somnifera* extracts.

8 Claims, No Drawings

WITHANIA SOMNIFERA DUNAL EXTRACTS FOR INCREASING MALE SPERM COUNT

This application met the requirements of 35 U.S.C. Section 371 on Nov. 9, 2001, and claims priority to PCT International Application PCT/JP00/02940 filed May 9, 2000, which in turn claims the benefit of Japanese application 11/128335, filed May 10, 1999.

TECHNICAL FIELD

The present invention relates to *Withania somnifera* (*Withania somnifera* Dunal.) which is known to be a medicinal plant.

*Withania somnifera* is also known as ashwagondha (ashvaganda), sekitome-hozuki, winter cherry, asganh, asunda, asarna, phatalfoda, askandha, achubagandi, amucrang kalang, amukila, kilzang (all phonetic), and so on.

BACKGROUND ART

It has come to be known of late that endocrine disturbing chemicals (environmental hormones) existing in our living environment, such as bisphenol A, dibutyl phthalate, vinclozolin, polychlorobiphenyls, ethynylestradiol, nonylphenol, etc., not to speak of dioxins, affect the reproductive functions of animals to reduce their sexual activities either reversibly or at times irreversibly and impair male genital organs causing decreases in sperm count, in particular. These endocrine disturbing chemicals are present in the environment and act at low concentrations so that they have become a social problem.

It is difficult, in the state of the art, to protect individuals from contaminations with such endocrine disturbing chemicals and all the countermeasures so far known are a negative measure which comprises measuring the concentrations of endocrine disturbing chemicals in foodstuffs and seeing to it that foods contaminated beyond tolerable concentration limits will be not ingested and a measure which comprises recommending the intake of diet fiber, chitin, chitosan, etc. which are expected to adsorb endocrine disturbing chemicals and let them be excreted as so adsorbed.

Meanwhile, *Withania somnifera* Dunal. is a tree of the genus Withania of the family Solanaceae, which is distributed in India and South Africa. It is a time-honored folk medicine or diet efficacious for sthenia, antirheumatism, antisenescence, and prophylaxis of marasmus in young children, among other indications (e.g. Kalpana Sharma and P. C. Dandiya; INDIAN DRUGS, 29 (6), 247–250) and, as such, has been used broadly.

As the constituents of *Withania somnifera*, alkaloids such as cuscohygrine, anahygrine, tropine, pseudotropine, anaferine, dl-isopellatierine, 3-tropyltigloate, withasomine, visamine, withaninine, withanine, pseudowithaninine, 3-alpha-tigloyloxytropane, choline, etc. and withanolides such as withaferin A, sitoindosides I-X, withanolide N, withanolide O, withanolide D, withanolide E, withanolide P, withanolide S, withanolide Q, withanolide R, withanolide G, withanolide H, withanolide I, withanolide J, withanolide K, withanolide U, withanolide Y, etc. are known.

DISCLOSURE OF INVENTION

The object of the present invention is to redress or relieve the effects of in vivo contaminations with endocrine disturbing chemicals and, as such, provide a composition and a food for promoting recovery of the reproductive function compromised by such chemicals.

After their intensive research, the inventors of the present invention found that *Withania somnifera* has an action to promote recovery of compromised reproductive function and have perfected the present invention.

The present invention, therefore, encompasses a composition for restoring compromised reproductive function or a composition for redressing atrophic or impaired genital organs, characterized in that it comprises *Withania somnifera*, and a composition for restoring compromised reproductive function or a composition for redressing atrophic or impaired genital organs, characterized in that it comprises an extract of *Withania somnifera*. Also encompassed is a compromised reproductive function-restorative composition or atrophic genital organ-redressing composition for restoration of the reproductive function compromised by endocrine disturbing chemicals.

Stated differently, the invention is concerned with the use of *Withania somnifera* for the production of a composition comprising *Withania somnifera* as the active ingredient for restoring compromised reproductive function; the use of *Withania somnifera* for the production of a composition comprising an extract of *Withania somnifera* as the active ingredient for restoring compromised reproduction function; a method of restoring compromised reproductive function which comprises giving a composition comprising *Withania somnifera* to an individual, and a method of restoring compromised reproductive function which comprises giving a composition comprising an extract of *Withania somnifera* to an individual.

In the present invention, *Withania somnifera* can be used regardless of whether it is a dried one or an undried one. And coarse cuttings or pulverizates of its root, leaf or whole plant can be orally taken or ingested as such or together with drinking matter such as water, lukewarm water, a fruit juice or milk. Alternatively, it can be judiciously extracted with hot water or an alcohol and the extract taken orally or ingested.

The extract of *Withania somnifera* can be obtained by treating fragments of the root, leaf or whole plant of *Withania somnifera* with a suitable extractant, such as water (hot water) or an alcohol, and subjecting the extract to concentration, optionally to dryness. This extract is preferably one containing not less than 1.0 weight % of alkaloids and not less than 1.0 weight % of withanolides, more preferably not less than 1.2 weight % of alkaloids and not less than 1.4 weight % of withanolides. The extract can be taken orally or ingested as it is or as suspended or dissolved in drinking matter such as water, lukewarm water, a fruit juice, tea or milk.

The dosage, ingestion amount or decoction amount (when a decocta is to be taken orally or ingested) of *Withania somnifera* for restoring compromised reproductive function is dependent on the recipient's sex and age, health status, and target organ or site but may appropriately be within the range of generally 1~100 g, preferably 2~20 g, as dry *Withania somnifera* per day per adult human. In the case of an extract, the daily amount per adult human is generally in the range of 0.1~10 g, preferably in the range of 0.2~5 g. In any event, the extract can be taken orally or ingested once daily or in 2~4 divided doses a day. The intake or ingestion time is not particularly restricted but may for example be before a meal, between meals, after a meal, or at bedtime. The composition can be taken orally or ingested together with a food.

The compromised reproductive function-restorative composition of the invention (hereinafter referred to as the composition of the invention) may be *Withania somnifera* or an extract thereof as such or a composition containing *Withania somnifera*, for example in the range of 0.01%~99.5%, preferably 0.5%~90%, in a physiologically acceptable, nontoxic and inert carrier.

As the carrier, a solid, semisolid or liquid diluent, a filler and one or more other formulation additives can be mentioned. The composition of the invention may be provided in any form such as neat powders, capsules, tablets, sugar-coated tablets, granules, powders, suspensions, solutions, syrups and drops, among others. Depending on cases, injectable forms may be employed.

The composition of the invention is useful for promoting recovery of compromised reproductive function in animals inclusive of man, particularly recovery of reproductive function in males. Furthermore, the composition of the invention is recommendable for promoting recovery of atrophic or impaired male genital organs. Therefore, the composition of the invention can be used in the field of medicine as a therapeutic or prophylactic drug.

In addition, the composition of the invention can be added to foods, namely general foods such as curry, pilaf, prepared dishes, etc. or other foods inclusive of drinks and cakes, or provided in such forms as tablets, capsules or granules for use as the so-called nutritional supplement or health food. Therefore, a compromised reproductive function-restorative food or atrophic genital organ-redressing food characterized by comprising *Withania somnifera*, a compromised reproductive function-restorative food or atrophic genital organ-redressing food characterized by comprising an extract of *Withania somnifera*, and such a compromised reproductive function-restorative food or atrophic genital organ-redressing food for restoring the reproductive function compromised by endocrine disturbing chemicals also fall within the scope of the present invention.

Stated differently, the above aspects of the invention are concerned with the use of *Withania somnifera* for the production of foods containing *Withania somnifera* as the active ingredient for restoring compromised reproductive function, the use of *Withania somnifera* for the production of foods containing an extract of *Withania somnifera* as the active ingredient for restoring compromised reproductive function, a method of restoring compromised reproductive function which comprises giving a food containing *Withania somnifera* to an individual, and a method of restoring compromised reproductive function which comprises giving a food containing an extract of *Withania somnifera* to a living body.

BEST MODE FOR CARRYING OUT THE INVENTION

The following example and test examples illustrate the present invention in further decaudal epididymis.

EXAMPLE 1
Preparation of an Extract

Ten (10) kg of the dried root of *Withania somnifera* Dunal. was washed thoroughly with water and, after drying, crushed into small pieces about 2~5 mm in diameter. To these pieces was added 10 volumes of 50% ethanol and an extraction was carried out under reflux at 60° C. for 4 hours. The resulting extract was concentrated to dryness under reduced pressure to give 50 g of a dry extract of *Withania somnifera*. Compositional analysis of this extract by HPTLC in accordance with the literature (BHATTACHARYA S. K. et al., PHYTOTHERAPY RESEARCH, 9, 110~113 (1995)) revealed that the total alkaloid content was 1.70 weight % and the withanolides content was 1.98 weight %.

Test Example 1
Compromised Reproductive Function-restoring Effect (1)

SD rats aged 11 weeks (in groups of 8) were orally dosed with 3 mg/kg of the endocrine disturbing chemical ethynylestradiol suspended in 0.5% sodium carboxymethylcellulose (CMC) solution (ethynylestradiol 0.6 mg/mL) or, as control, 5 mL/kg of 0.5% CMC solution once daily in the morning for 2 weeks, and after the administration course, the testis, epididymis, prostate and seminal vesicle were respectively weighed. The results are shown in Table 1.

TABLE 1

|  | Testis | Epididymis | Seminal vesicle | Prostate |
| --- | --- | --- | --- | --- |
| CMC-dosed group | 836.1 ± 51.3 | 250.9 ± 13.8 | 343.8 ± 35.9 | 212.7 ± 39.3 |
| Ethynylestradiol-dosed group | 705.4* ± 67.9 | 117.5* ± 7.5 | 88.1* ± 23.7 | 77.4* ± 17.6 |

*: $p < 0.05$ (Student's t-test), n = 8 (ng/100 gBW)

It is clear from Table 1 that the rat genital organs atrophied owing to the influence of the endocrine disturbing chemical.

Then, the above rats (in groups of 8) with the reproductive function compromised by the endocrine disturbing chemical were orally dosed with 5 mL/kg of 2% gum arabic solution or either 100 mg/kg (*Withania somnifera* 20 mg/mL) or 500 mg/kg (*Withania somnifera* 100 mg/mL) of the dry extract of *Withania somnifera* according to Example 1 as suspended in 2% gum arabic solution once daily in the morning for 2 weeks, and the degrees of recovery of reproductive function due to *Withania somnifera* were evaluated. The results are shown in Table 2.

TABLE 2

|  | Testis | Epididymis | Seminal vesicle | Prostate |
| --- | --- | --- | --- | --- |
| Gum arabic-dosed group | 596.8 ± 86.6 | 119.5 ± 15.1 | 171.5 ± 65.9 | 116.2 ± 28.9 |
| Withania somnifera 100 mg/kg-dosed group | 581.1 ± 60.2 | 116.2 ± 10.7 | 229.7* ± 30.2 | 131.4 ± 15.8 |
| Withania somnifera 500 mg/kg-dosed group | 618.5 ± 97.8 | 124.7 ± 13.3 | 207.7 ± 44.3 | 123.8 ± 29.2 |

*: $p < 0.05$ (Dunnett t-test), n = 8 (mg/100 gBW)

It is clear from Table 2 that the group dosed with *Withania somnifera* showed a recovery of the genital organs, particularly the seminal vesicle and prostate, which had atrophied owing to the influence of the endocrine disturbing chemical. Rat husbandry conditions: room temperature 21~25° C., humidity 45~60%, artificial lighting 12 hrs (7:00 a.m.~7:00 p.m.), ventilation frequency 15/hr, solid food (CE-2, CLEA Japan Inc.) and drinking water ad libitum.

Test Example 2
Compromised Reproductive Function-restoring Effect (2)

Slc:SD rats aged 10 weeks (in groups of 10) were orally dosed with 3 mg/kg of the endocrine disturbing chemical ethynylestradiol suspended in 0.5% sodium carboxymethylcellulose (CMC) solution (ethynylestradiol 0.3 mg/mL) or, as control, 10 mL/kg of 0.5% CMC solution once daily in the morning for 10 days, and at 1 week after the administration course, the testis, epididymis, prostate and seminal vesicle were respectively weighed. The results are shown in Table 3.

TABLE 3

|  | Testis | Epididymis | Seminal vesicle | Prostate |
|---|---|---|---|---|
| CMC-dosed group | 863.1 ± 63.5 | 246.9 ± 18.4 | 337.5 ± 28.4 | 203.6 ± 20.7 |
| Ethynylestradiol-dosed group | 731.3* ± 53.6 | 154.5* ± 21.0 | 170.0* ± 33.1 | 102.3* ± 19.9 |

*: $p < 0.05$ (Student's t-test), n = 10 (mg/100 gBW)

It is apparent from Table 3 that the rat genital organs atrophied under the influence of the endocrine disturbing chemical.

Then, the above rats with the reproductive function compromised by the endocrine disturbing chemical (in groups of 10) were orally dosed with 10 mL/kg of 2% gum arabic solution or 100 mg/kg of the dry extract of *Withania somnifera* according to Example 1 as suspended in 2% gum arabic solution (*Withania somnifera* 10 mg/mL) once daily in the morning for 4 weeks, and the degrees of recovery of reproductive function due to *Withania somnifera* were evaluated. The results are shown in Table 4.

TABLE 4

|  | Testis | Epididymis | Seminal vesicle | Prostate |
|---|---|---|---|---|
| Gum arabic-dosed group | 781.2 ± 100.9 | 195.7 ± 22.3 | 317.9 ± 26.7 | 204.7 ± 30.8 |
| Withania somnifera 100 mg/kg-dosed group | 799.1 ± 60.2 | 222.1* ± 18.3 | 326.6 ± 52.6 | 239.3 ± 47.9 |

*: $p < 0.05$ (Dunnett t-test), n = 10 (mg/100 gBW)

It is apparent from Table 4 that compared with the control group (gum arabic-dosed group), the *Withania somnifera*-dosed group showed an accelerated recovery of the atrophic or impaired genital organs caused by the endocrine disturbing chemical, with a significant difference for the epididymis.

Rat husbandry conditions: room temperature 21~25° C., humidity 45~60%, artificial lighting 12 hrs (7:00 a.m.~7:00 p.m.), ventilation frequency 15/hr, solid food (CE-2, CLEA Japan Inc.) and drinking water ad libitum.

Test Example 3
Sperm Count and Motile Sperm Rate

Using rats with the genital organs impaired by ethynylestradiol as in Test Example 2, the sperm count and motile sperm rate were investigated. The results are shown in Table 5.

TABLE 5

|  | Caudal epididymis (weight, g) | Sperm count (x$10^6$) | Sperm count /caudal epididymis (x$10^6$) | Sperm count/ epididymis (x$10^6$) | Motile sperm rate (%) |
|---|---|---|---|---|---|
| CMC-dosed group | 0.190 ± 0.017 | 110.3 ± 18.1 | 580.6 ± 79.0 | 565.2 ± 81.0 | 74.7 ± 8.0 |
| Ethynylestradiol-dosed group | 0.076 ± 0.011 | 13.0* ± 12.7 | 160.2* ± 147.2 | 88.8* ± 87.4 | 40.6* ± 30.0 |

*: $p < 0.05$ (Student's t-test), n = 10

Then, the above rats with the reproductive function compromised by the endocrine disturbing chemical (in groups of 10) were orally dosed with 10 mL/kg of 2% gum arabic solution or 100 mg/kg of the dry extract of *Withania somnifera* according to Example 1 as suspended in 2% gum arabic solution (*Withania somnifera* 10 mg/mL) once daily in the morning for 4 weeks and, after the administration course, the sperm count and motile sperm rate in each rat were determined by the following methods.

(1) Method for Determination of Motile Sperm Rate

From the right epididymis, the caudal epididymis was excised and weighed with Sartorius electronic balance LC620-S. The caudal epididymis was placed in a sperm collection vial containing 5 mL of BSA-Hanks solution and cut 3 times to cause the sperm to swim out. A 0.05 mL portion of the sperm fluid was sampled and diluted with 0.95 mL of BSA-Hanks solution for use as a diluted sperm fluid. The number of non-motile sperms in the diluted sperm fluid was determined with Thoma's hemocytometer. After this counting of non-motile sperms, the vessel containing the diluted sperm fluid was immersed in hot water and, after return to room temperature, the sperms were counted with the hemocytometer. When the sperm population in the sperm fluid was found to be small (low turbidity) by gross observation, an aliquot of the fluid was taken as a motile sperm counting sample fluid and the above measurement was carried out. Using the measured values, the motile sperm rate was calculated by means of the following equation [1].

Motile sperm rate (%)=(number of sperms−number of non-motile sperms)/number of sperms×100　　　[1]

(2) Method for Determination of Sperm Count

The caudal epididymis in the sperm collection vial used in the above procedure (1) was further cut to release sperms and the fluid in the vial was filtered through a nylon-mesh sieve. The stock filtrate, 0.1 mL, was diluted with 1.9 mL of formalinized saline and the number of sperms was determined with Thoma's hemocytometer. When the sperm population in the sperm sample was considered to be too small (low turbidity), the stock sperm fluid was not diluted but the vessel was directly immersed in hot water and, after reutrn to room temperature, the number of sperms was determined. Moreover, the number of sperms (sperm count) per caudal epididymis was calculated using the number of sperms determined and the dilution factor by means of the equation given below, with the value per caudal epididymis unit weight (g) being taken as the sperm count/caudal epididymis and the value per epididymis as the sperm count/epididymis. Sperm count=measured number of sperms×dilution factor Number of sperms/caudal epididymis=number of sperms determined×dilution factor/weight of the caudal epididymis epididymis (g)

Number of sperms/epididymis=(number of sperms/caudal epididymis)×weight of epididymis (g)

The results of the above test are shown in Table 6.

TABLE 6

|  | Caudal epididymis (weight, g) | Sperm count (x$10^6$) | Sperm count /caudal epididymis (x$10^6$) | Sperm count/ epididymis (x$10^6$) | Motile sperm rate (%) |
|---|---|---|---|---|---|
| Gum arabic-dosed group | 0.153 ± 0.024 | 78.4 ± 34.8 | 493.4 ± 180.9 | 437.2 ± 185.9 | 55.9 ± 19.7 |
| Withania sominfera 100 mg/kg-dosed group | 0.172 ± 0.022 | 101.4 ± 39.4 | 577.6 ± 171.1 | 541.5 ± 187.4 | 57.1 ± 19.4 |

*: $p < 0.05$ (Dunnett t-test), n = 10

It is apparent from Table 6 that in the sperm count and motile sperm rate depressed by the endocrine disturbing chemical, too, early recoveries were obtained as compared with control.

What is claimed is:

1. A method for increasing decreased sperm count in a male, comprising administering an effective amount of an alcohol and/or aqueous extract of a root, leaf or whole plant of *Withania somnifera* Dunal to a male subject in need of such treatment, wherein said decreased sperm count is caused by an endocrine disturbing chemical.

2. The method of claim 1, wherein the extract is an aqueous extract.

3. The method of claim 1, wherein the extract is an alcohol extract.

4. The method of claim 3, wherein the alcohol is ethanol.

5. A method for increasing decreased sperm count in a male, comprising administering an effective amount of a food supplement comprising a food and an aqueous and/or alcohol extract of *Withania somnifera* Dunal to a male subject in need of such a treatment, wherein said decreased sperm count is caused by an endocrine disturbing chemical.

6. The method of claim 5, wherein the extract is an aqueous extract.

7. The method of claim 5, where the extract is an alcohol extract.

8. The method of claim 7, wherein the alcohol is ethanol.

* * * * *